(12) United States Patent
Wang et al.

(10) Patent No.: US 12,064,600 B2
(45) Date of Patent: Aug. 20, 2024

(54) ACOUSTIC METHOD FOR PRECISELY CONTROLLING AND METERING THE MANUAL INJECTION DOSAGE

(71) Applicant: Phray Technology Co., Ltd., Henan (CN)

(72) Inventors: Yongxin Wang, Henan (CN); Leijie Wang, Henan (CN); Jucai Fang, Henan (CN); Yanling Liu, Henan (CN); Weidong Zhang, Henan (CN); Wuyi Ming, Henan (CN); Shengfei Zhang, Henan (CN)

(73) Assignee: Phray Technology Co., Ltd., Zhengzhou (CN)

( * ) Notice: Subject to any disclaimer, the term of this patent is extended or adjusted under 35 U.S.C. 154(b) by 22 days.

(21) Appl. No.: 18/122,012

(22) Filed: Mar. 15, 2023

(65) Prior Publication Data

US 2023/0347052 A1 Nov. 2, 2023

(30) Foreign Application Priority Data

Apr. 29, 2022 (CN) .......................... 202210465130.7

(51) Int. Cl.
*A61M 5/172* (2006.01)
*A61M 5/24* (2006.01)
*A61M 5/32* (2006.01)

(52) U.S. Cl.
CPC ........ *A61M 5/1723* (2013.01); *A61M 5/2422* (2013.01); *A61M 5/3204* (2013.01);
(Continued)

(58) Field of Classification Search
None
See application file for complete search history.

(56) References Cited

U.S. PATENT DOCUMENTS

| 10,232,123 | B1 * | 3/2019 | Binier | G16H 20/17 |
| 2013/0079727 | A1 * | 3/2013 | Schildt | A61M 5/24 |
| | | | | 604/207 |

(Continued)

FOREIGN PATENT DOCUMENTS

CN  106150716  * 11/2016

OTHER PUBLICATIONS

Cn 106150716A translation (Year: 2016).*

*Primary Examiner* — Manuel A Mendez

(57) ABSTRACT

Disclosed is an acoustic method for precisely controlling and metering manual injection. The method includes: rotating a main housing to allow ratchet grooves to collide with ratchets on a ratchet wheel; obtaining collision voice and vibration signals by a switch sensor and a perception sensor; performing a Mel-frequency cepstral coefficient (MFCC) algorithm and classification with deep neural networks (DNN) on signals detected by a voice sensor, to output processed and recognized voice features; performing an empirical mode decomposition (EMD) algorithm and classification with cyclic delay diversity (CDD) on signals detected by a vibration sensor, to output processed and recognized vibration signals; and inputting the output voice features, the vibration signals, and reception time differences between the voice signals and the vibration signals into a support vector machine (SVM) classifier jointly for final recognition and classification, to recognize whether manual injection is correctly performed.

8 Claims, 8 Drawing Sheets

(52) U.S. Cl.
CPC ............... *A61M 2205/3375* (2013.01); *A61M 2205/582* (2013.01)

(56) References Cited

U.S. PATENT DOCUMENTS

2016/0082197 A1\* 3/2016 Giambattista ..... A61M 5/31551
604/211
2022/0120026 A1\* 4/2022 Mashal ................... D06F 34/18

\* cited by examiner

ACOUSTIC METHOD FOR PRECISELY CONTROLLING AND METERING THE MANUAL INJECTION DOSAGE

CROSS-REFERENCE TO RELATED APPLICATION

This application claims priority from the Chinese patent application 202210465130.7 filed Apr. 29, 2022, the content of which is incorporated herein in the entirety by reference.

TECHNICAL FIELD

The present disclosure belongs to the field of insulin injection metering, and particularly relates to an acoustic method for precisely controlling and metering manual injection.

BACKGROUND

An insulin injection device is designed to infuse insulin to a patient by simulating secretion of the insulin in a healthy person. In order to effectively regulate blood glucose, a diabetic patient needs to carry the insulin injection device all the time even in exercise and sleep, except bathing and some special conditions. As the insulin injection device advances, syringes, insulin jet injectors, insulin pumps, insulin pens, etc. successively emerge. The syringes are conventional insulin injection devices that vary in volume and have needles different in length and diameter. Disadvantageously, such an injection device is only applicable to patients with sharp vision and flexible hands and inconvenient to carry, and its syringe needle will cause pain to the skin. The insulin pen, a pen-type insulin injection device, is a revolutionary breakthrough in the field of diabetes treatment. Similar to a pen in shape, the insulin pen is slightly larger, which can reduce the psychological burden of insulin injection on patients. Its internal structure is unique, with insulin and an injection device combined integrally.

The insulin pen has the following advantages over conventional syringes: (1) integration of the insulin and injection device eliminates a cumbersome process of extracting insulin, and a refill is easy to replace; (2) the portability is excellent; (3) operation is simple and flexible; (4) an injection process is simpler and hidden; (5) the dosage is more accurate, with a minimum infusion unit of 0.1 u; and (6) less pain is caused.

The insulin pen generally has two injection ways: one way is manual injection, that is to say, insulin is injected into the patient's own body manually, which is cumbersome as it requires intense concentration of the patient so as to prevent over-dosage and under-dosage; and the other way is automatic injection, which relies on relevant devices and audible and visual reminders to inject insulin and cannot be used normally with a dead battery in the open.

When insulin is injected manually without power, the insulin dosage of daily injection may be inaccurate. Injecting insulin into the patient's own body manually is cumbersome as it requires intense concentration of the patient so as to prevent over-dosage and under-dosage. Therefore, a daily metering method for manual injection of insulin is extremely important.

Disclosed in a Chinese invention patent (Application No. 202111070240.5, Publication No. CN 113730729A) are a manual-electric integrated insulin pen and an injection method therefor. In use, the pen still has the following defects: it is difficult to accurately determine a manual injection metering cycle during manual operation, and the volumes of collision sounds between a ratchet wheel and a ratchet groove are different (due to influence from the depth of ratchet groove, the service life of the insulin pen, the season for injecting insulin and the ambient temperature for injecting insulin, etc.), so the accuracy of manual injection is not high enough yet. Moreover, manual injection requires intense concentration on counting the frequency of the collision sound between the ratchet wheel and the ratchet groove (the injection dosage can be inferred from the prompt of the sound). As a result, elderly patients are prone to counting errors during independent operation.

SUMMARY

In order to solve the defects of the prior art, the present disclosure provides an acoustic method for precisely controlling and metering manual injection, which has high injection dosage accuracy, automatic metering and wide applicability.

In order to solve the above technical problem, the following technical solution is used in the present disclosure. The acoustic method for precisely controlling and metering manual injection includes:

A, making an injection pen enter an energy-saving mode when power is less than 20%, to allow manual injection operation merely; and when a user picks up the injection pen, sending a signal to a controller by a perception sensor arranged on a left side of an inner wall of a main housing, and receiving, by the controller, a signal of using the injection pen;

B, removing a pen cap and a needle cap, and pushing a metering ring leftwards, to separate the metering ring from a left end of the main housing, separate all clamping blocks from slots, and move an outer triangular ridge of a left side edge of each elastic clamping plate leftwards to a right side of a corresponding sector-shaped limit plate, where the main housing rotates relative to a second connection sleeve and a refill in this case; and monitoring that the metering ring moves leftwards and transmitting a signal to the controller by a switch sensor arranged on the left side of the inner wall of the main housing, and receiving the signal by the controller, to start a manual injection mode;

C, penetrating a needle into a human body by a user, holding a refill sleeve and the metering ring with one hand, holding the main housing with the other hand, rotating the main housing, to make the main housing drive an internal gear box to rotate, where a power output shaft of the gear box is in a locked state in this case, driving a screw rod to rotate by the power output shaft of the gear box, driving a hollow push rod in threaded connection to the screw rod by the screw rod to move leftwards, pushing an injection piston by the hollow push rod to move leftwards in the refill, and injecting an insulin solution to be injected in the refill into the human body by the injection piston;

D, during rotation of the main housing, making a reverse rotation stopper arranged on the inner wall of the main housing rotate relative to the ratchet wheel, generating collision sounds and vibration simultaneously by ratchet grooves on an inner circle of the reverse rotation stopper and ratchets on an outer circle of the ratchet wheel, where a sound sensor and a vibration sensor are arranged inside the ratchet wheel, collecting each collision sound signal by the sound sensor, collecting each vibration signal by the vibration sensor, transmitting the collected signals to the controller by the sound sensor and the vibration sensor, and classifying and recognizing the sound and vibration signals by the controller through an internal algorithm, to record and save an insulin solution injection dosage, where each recognition success represents injection of 0.5 u of insulin solution, so as to accurately calculate the injection dosage during manual injection; and displaying the injection dosage on a display screen, such that the user can be informed of the injection dosage only by observing a numerical value on the display screen; and E, after a target injection dosage is reached, stopping rotating the main housing, moving the metering ring rightwards, and resetting the metering ring, so as to clamp all the clamping blocks correspondingly into the slots, and further to keep the main housing and the refill fixed; and closing the needle cap and pen cap.

The inner circle of the reverse rotation stopper is uniformly provided with nine ratchet grooves circumferentially, a central angle between two adjacent ratchet grooves is 40°, the nine ratchet grooves are divided into three groups in the same sequence, that is, group 1, group 2 and group 3, three adjacent ratchet grooves serve as one group, depths of the three ratchet grooves of each group are different and successively increase in a clockwise direction, arrangement of the depths of the ratchet grooves of the three groups is consistent, the outer circle of the ratchet wheel is uniformly provided with three ratchets circumferentially, a central angle between two adjacent ratchets is 120°, when the ratchet wheel rotates, the three ratchets collide with the ratchet grooves of the same depth simultaneously, and the sounds and vibration generated by collisions between the ratchet grooves and the ratchets are different every 40° of rotation of the ratchet grooves; and in step D, the internal algorithm of the controller includes performing feature processing separately on the sound signals and the vibration signals generated when the ratchet grooves on the inner circle of the reverse rotation stopper collide with the ratchets on the outer circle of the ratchet wheel, performing processing with internal algorithm of the controller and classification and recognition with neural networks, and then uploading a recognition result of the sound signals, a recognition result of the vibration signals and detection time differences between the sound signals and the vibration signals to a support vector machine (SVM) separately for classification and recognition again.

A Mel-frequency cepstral coefficient (MFCC) method is used for a feature processing method of the sound signals generated when the ratchet grooves on the inner circle of the reverse rotation stopper collide with the ratchets on the outer circle of the ratchet wheel, an MFCC is extracted based on a Mel frequency, and a mapping relation between the Mel frequency and a normal Hertz frequency is shown in equation (1):

$$f_{mel} = 2595 \log_{10}\left(1 + \frac{f}{700}\right) \quad (1)$$

where $f_{inel}$ represents a Mel frequency in unit of MEL, and f represents a linear frequency in unit of Hz;

a particular flow of the Mel-frequency cepstral coefficient (MFCC) method includes:

1) collecting the sound signals: when the ratchet grooves collide with the ratchets on the outer circle of the ratchet wheel, transmitting the sound signals of the collision sounds to the interior of the controller by means of the sound sensor arranged in the ratchet wheel, where a collection time of each sound signal is 0.2 s-0.5 s;

2) pre-processing the sounds: where a pre-processing process mainly includes performing pre-emphasis, framing and windowing on the sound signals; where the pre-emphasis on the sound signals usually uses a filtering method, in which an input signal x(n) passes through a high-pass filter, the filter is expressed as $V(n)=x(n)-a1x(n-1)$ in a time domain and expressed as $H(z)=1-a_1 z^{-1}$ in a frequency domain, where $0.9 \leq a_1 \leq 1.0$, and $a_1$ is a pre-emphasis coefficient and is preferably 0.97;

during the framing, a "short-time stationarity feature" of the sound signals is used to decompose each signal into several frames, each frame can be set as 20 ms, and a previous frame and a next frame overlap in half; and after the framing, the time domain signal x(n) is combined into $x_i(n)$, where i represents the relative frame number; and the windowing is to multiply an original function by a window function; assuming that x(n) is a time domain signal and w(n) is a window function, an N-point sequence $x_n(n)$ is derived from truncation of x(n) by w(n), as shown in equation (2):

$$x_n(n) = w(n)x(n) \quad (2)$$

the present patent uses a Hamming window, as shown in equation (3) below:

$$W(n, a_2) = (1 - a_2) - a_2 \times \cos\left[\frac{2\pi n}{N-1}\right] \quad (3)$$

where $W(n, a_2)$ represents the window function, n=1, 2, 3, ......, N represents a serial number of a sampling point of the window function, and $a_2$ represents a middle position of a window and is preferably 0.46;

3) performing fast Fourier transform (FFT): performing FFT on $x_i(n)$ to obtain $X_i(K)$, and obtaining computational equation (5) of $X_i(K)$ by combining equation (2) and computational equation (4) of discrete Fourier transform (DFT), where a Hamming window is used:

$$X_n\left(e^{j\frac{2kn}{N}}\right) = X_N(k) = \sum_{0}^{N-1} x(n)e^{-j\frac{2\pi kn}{N}}, \quad (4)$$

$$k = 0, 1, 2, \ldots, N-1$$

$$X_i(k) = \sum_{0}^{N-1} x_i(n)h(n)e^{-j\frac{2\pi km}{N}}, \quad (5)$$

$$k = 0, 1, \ldots, N-1$$

where in equation (4), x(n) represents an original signal, X N (k) represents a coefficient after discrete cosine transform (DCT), and N represents the number of points of the original signal; and in equation (5), N represents a length of DFT, k represents a frequency, and h(n) represents a window function having the same length as the sample;

4) determining a Mel filter bank: where the Mel frequency filter bank is a combination of a plurality of triangular band-pass filters $H_m(k)$ arranged according to a rule within a specified frequency spectrum range of an acoustic signal, $0 \leq m \leq M$, M is the number of filters, the number of filters is usually between 24-40, a center frequency of each of the triangular filters is f(m), and transfer function equation (6) is as follows:

$$H_m(k) = \begin{cases} \dfrac{k - f(m-1)}{f(m) - f(m-1)}, & f(m-1) \le k \le f(m) \\ \dfrac{f(m+1) - k}{f(m+1) - f(m)}, & f(m) \le k \le f(m+1) \\ 0, & k < f(m-1) \mid k > f(m+1) \end{cases} \quad (6)$$

where $H_m(k)$ is a frequency response of the Mel filters, and M is preferably 24;

5) computing logarithmic energy: in order to make a Mel frequency spectrum obtained by means of the Mel filter bank more robust to noise and spectral estimation errors, computing the logarithmic energy of the Mel frequency spectrum, where transfer function equation (7) from a linear frequency spectrum to a logarithmic frequency spectrum is as follows:

$$S(m) = ln(\Sigma_0^{N-1} |X(k)|^2 H_m(k))(0 \le m \le M) \quad (7)$$

where X(k) is a linear frequency spectrum, S(m) is a logarithmic frequency spectrum, and m is the number of triangular band-pass filters;

6) performing discrete cosine transform: performing discrete cosine transform (DCT) on the obtained logarithmic frequency spectrum S(m) to be converted into the time domain, where the time domain is a cepstrum domain in this case, so as to obtain the Mel-frequency cepstral coefficient, and computational equation (8) thereof is as below:

$$C(n) = \sum_0^{M-1} S(m) \ne \cos\left(\dfrac{\pi n(m - 0.5)}{M}\right), \quad (8)$$
$$0 \le n \le L$$

where C(n) represents the MFCC of the nth filter, and L represents the dimension for extracting the feature parameter MFCC; M represents the number of the Mel filter banks; and the above is a flow for extracting the Mel-frequency cepstral coefficient (MFCC); and 7) performing classification with deep neural networks (DNN): inputting static features of the MFCC from acoustic detection into a deep neural networks (DNN) model, outputting a recognition result, and recording signals of the sound signals subjected to final processing and recognition as sound 1, sound 2, sound 3 and sound 4 separately, sound 1 being a coefficient of a sound generated by a collision between the ratchet groove with the largest depth and the ratchet wheel, sound 2 being a coefficient of a sound generated by a collision between the ratchet groove with the second largest depth and the ratchet wheel, sound 3 being a coefficient of a sound generated by a collision between the ratchet groove with the least depth and the ratchet wheel, and sound 4 being a coefficient of a sound generated by other external collisions; and training samples based on the deep neural networks, where factors of the samples include the depths of the ratchet grooves, service life of an insulin syringe, a season for injecting insulin, an ambient temperature for injecting insulin, etc., training 2000 groups of samples, and training 500 groups of each of sound 1, sound 2, sound 3 and sound 4 samples; where the deep neural networks (DNN) model is a conventional model and will not be repeated herein.

An empirical mode decomposition (EMD) method is used as a feature processing method of the vibration signals generated when the ratchet grooves on the inner circle of the reverse rotation stopper collide with the ratchets on the outer circle of the ratchet wheel, EMD decomposes a signal according to time scale features of the signal without setting a basis function, which is essentially a time-frequency analysis method, and is mainly used to complete decomposition of a non-stationary signal, to obtain a linear sum of a plurality of intrinsic mode functions (IFMs) and a trend term after decomposition, and the non-stationary signal y(t) may be expressed as:

$$y(t) = \sum_0^n IMF_i(t) + r(t) \quad (9)$$

where $IMF_i(t)$ represents an ith order intrinsic mode function, and r(t) is a low-frequency pulsation, that is, the trend term; and a particular flow of the empirical mode decomposition (EMD) method includes performing classification on one vibration signal in sequence with EMD and a convolution neural network (CNN).

Particular steps for performing EMD on a signal include:

(1) collecting the vibration signals: when the ratchet grooves collide with the ratchets on the outer circle of the ratchet wheel, transmitting the vibration signals of collisions to the interior of the controller by means of the vibration sensor arranged in the ratchet wheel, where a collection time of each vibration signal is 0.2 s-0.5 s;

(2) finding out all maximum value points and minimum value points of the vibration signals y(t), connecting all the maximum value points and minimum value points with curves to obtain an upper envelope line $e_{max}(t)$ and a lower envelope line $e_{min}(t)$, and computing a mean envelope function d(t) of the upper envelope line and the lower envelope line;

$$d(t) = \dfrac{e_{max}(t) + e_{min}(t)}{2} \quad (10)$$

(3) recording a difference between y(t) and d(t) as $h_1(t)$ by Equation (10), and under the condition that $h_1(t)$ is not one IMF, continuing the above process until $h_{1k}(t)$ in a kth cycle is one IMF, which is recorded as $c_1(t)$;

(4) obtaining remaining signals $y_1(t)$ according to the decomposed IMF; and $$y_1(t) = y(t) - c_1(t) \quad (11)$$

(5) repeating the above steps until an nth-order $h_n(t)$ becomes a monotonic sequence, and defining the trend term $r_n(t)$ as $y_n(t)$.

A particular process for performing classification with a convolution neural network (CNN) includes: inputting vibration pre-processing signal from vibration detection into a convolution neural network (CNN) model, outputting a recognition result, and recording signals recognized of the vibration signals subjected to final processing and recognition as vibration 1, vibration 2, vibration 3 and vibration 4 separately, vibration 1 being a vibration processing signal generated by a collision between the ratchet groove with the largest depth and the ratchet wheel, vibration 2 being a vibration processing signal generated by a collision between the ratchet groove with the second largest depth and the ratchet wheel, vibration 3 being a vibration processing signal generated by a collision between the ratchet groove with the least depth and the ratchet wheel, and vibration 4 being a vibration processing signal generated by other external collisions; and training samples based on the deep neural networks, where factors of the samples include the depths of the ratchet grooves, service life of an insulin syringe, a season for injecting insulin, an ambient temperature for injecting insulin, etc., training 2000 groups of samples, and training 500 groups of each of vibration 1, vibration 2, vibration 3 and vibration 4 samples; where the convolution neural network (CNN) model is a conventional model and will not be repeated herein.

The uploading a recognition result of the sound signals, a recognition result of the vibration signals and detection time differences T between the sound signals and the vibration signals to a support vector machine (SVM) separately for classification and recognition again specifically includes:

since various kinds of sound signals and vibration signals exist in a process of manual injection of insulin, a multi-classification problem is involved, in a process of sound detection and vibration detection, training samples of a SVM model according to the actual situation due to different fundamental frequency periods of the sound signals and the vibration signals, training the samples based on the SVM model, where the factors of the samples include the depths of the ratchet grooves, the service life of an insulin syringe, a season for injecting insulin, the detection time differences T between the sound signals and the vibration signals, the ambient temperature for injecting insulin, etc., and training 2000 groups of samples; and inputting sound 1, sound 2, sound 3 and sound 4 of the sound signals subjected to final processing and recognition and vibration 1, vibration 2, vibration 3 and vibration 4 of the vibration signals subjected to final processing and recognition into the SVM model, further inputting the detection time differences T between the sound signals and the vibration signals into the SVM model, and outputting results by means of recognition by the SVM model, where the results include normal injection information, other syringe injection information and invalid injection information, so as to guarantee that the manual injection of insulin is accurately metered; where a manual injection metering cycle involves two situations, in the first situation, the cycle includes an entire time period from turning on of the switch sensor to turning off of the switch sensor, and in the second situation, after reception of a signal that the switch sensor is turned on, the manual injection mode of a manual injection device is not ended due to other situations, and the perception sensor automatically ends metering when perceiving no external human contact in 10 minutes; and an injection dosage of insulin per time is shown in Equation 12:

$$S = 0.5 b_1 + b_2 \times 0 \quad (12)$$

where S is an injection dosage per injection cycle, $b_1$ is the number of detection recognition of the injection device, and $b_2$ is the number of invalid detection recognition.

The first situation is as follows: when using the insulin injection device for manual injection, a user removes the pen cap and the needle cap before use, and then pushes the metering ring leftwards, to separate the metering ring from the left end of the main housing, and in this case, the switch sensor transmits a manual injection start signal, to start the injection cycle; and after manual injection is completed, the patient pushes the metering ring rightwards, to attach the metering ring to the left end of the main housing, and in this case, the switch sensor transmits a manual injection end signal, to end the injection cycle; and the second situation is as follows: when using the insulin injection device for manual injection, a patient removes the pen cap and the needle cap before use, and then pushes the metering ring leftwards, to separate the metering ring from the left end of the main housing, and in this case, the switch sensor transmits a manual injection start signal, to start the injection cycle; and when the patient has an emergency during injection, manual injection is not completed and the manual injection mode is not ended, and in this case, the perception sensor automatically ends the metering cycle when perceiving no touch on the injection device in 10 minutes by the patient.

With the above technical solution, when insulin needs to be manually injected, the switch sensor and the perception sensor may detect a state of the injection device; a Mel-frequency cepstral coefficient (MFCC) algorithm and classification with deep neural networks (DNN) are performed on signals detected by a sound sensor, to output processed and recognized sound features; an empirical mode decomposition (EMD) algorithm and classification with cyclic delay diversity (CDD) are performed on signals detected by a vibration sensor, to output processed and recognized vibration signals; and the output sound features, the vibration signals, and reception time differences between the sound signals and the vibration signals are input into a support vector machine (SVM) classifier jointly for final recognition and classification, to recognize whether manual injection is correctly performed, such that the manual injection may be accurately metered.

According to the present disclosure, algorithms used for classifying and recognizing sounds and vibrations are designed scientifically. Sound and vibration signals generated during manual injection may be intelligently collected and recognized, so as to record an insulin injection dosage more precisely, and the use is more convenient with better applicability.

Figure 1:
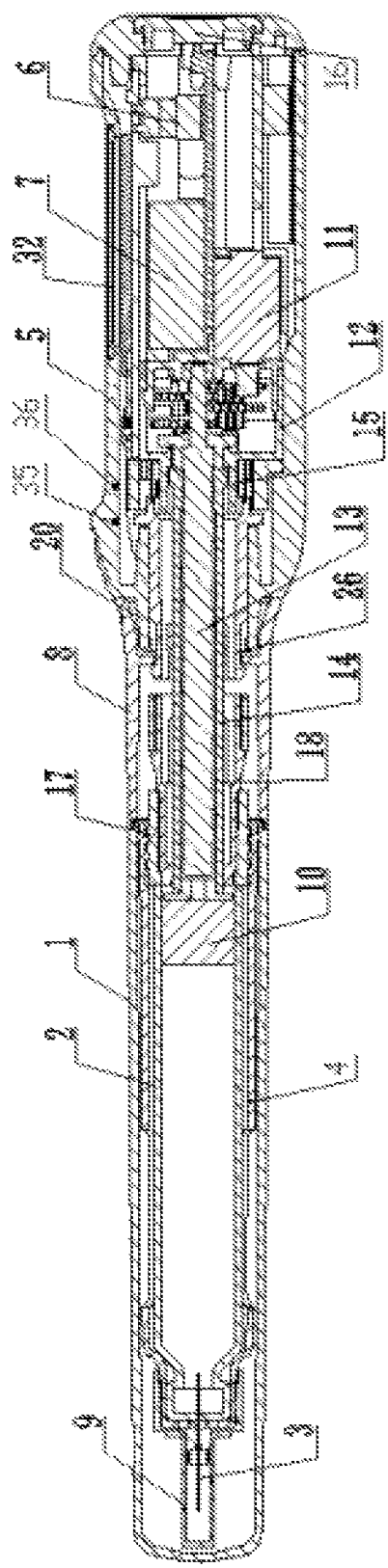
FIG. 1 is a sectional view of a structure of an injection pen according to the present disclosure.
Figure 2:
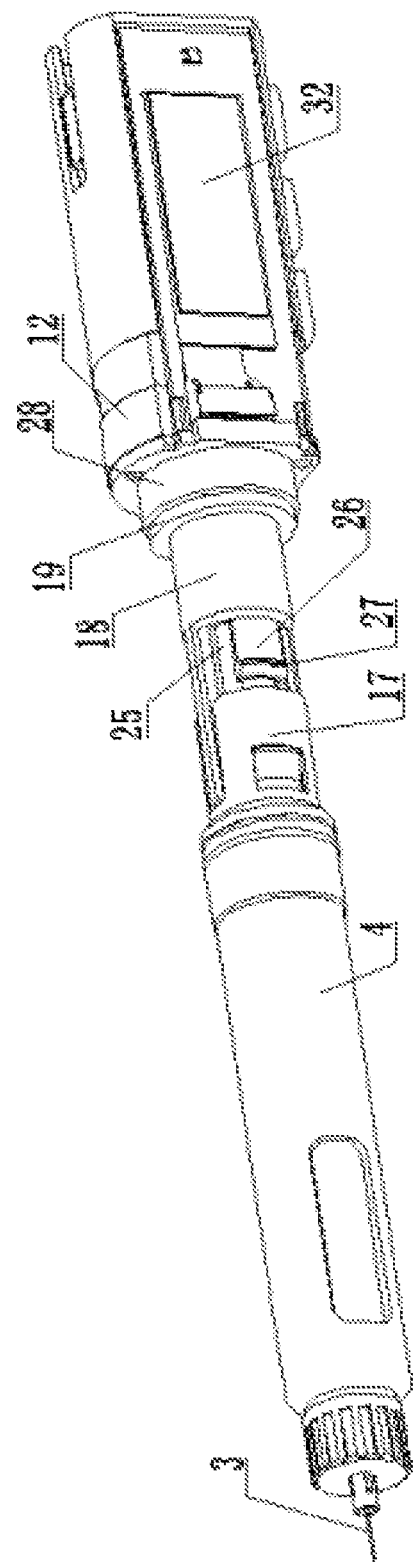
FIG. 2 is an axonometric view of an overall structure of an injection pen with a main housing and a metering ring removed.
Figure 3:
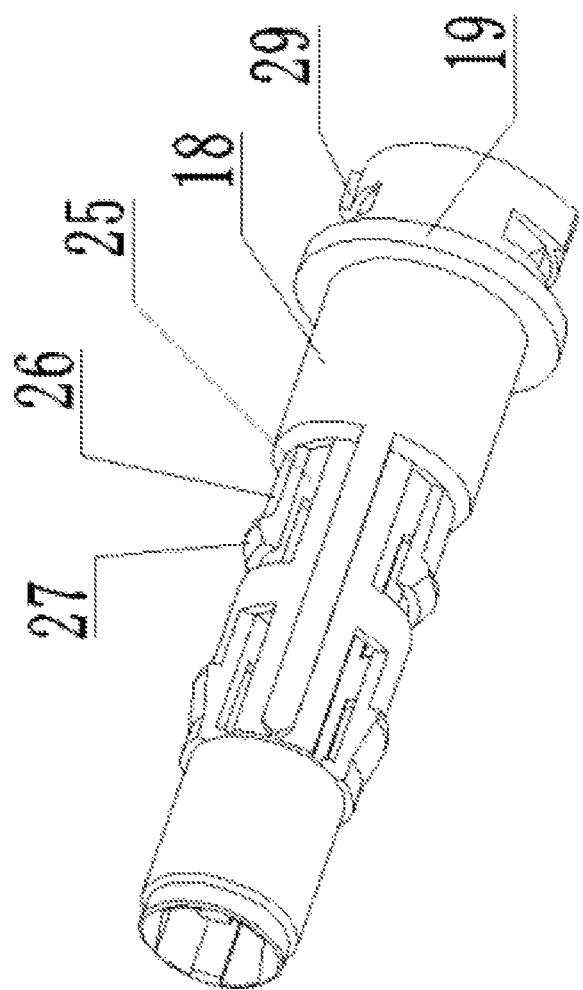
FIG. 3 is an axonometric view of a second connection sleeve of an injection pen.

Reference numerals in FIGS. 1-5: pen cap 1, refill 2, needle 3, refill sleeve 4, main housing 5, controller 6, miniature battery, metering ring 8, needle cap 9, injection piston 10, electric motor 11, gear box 12, screw rod 13, hollow push rod 14, tubular column 15, switch key 16, first connection sleeve 17, second connection sleeve 18, ring-shaped limit plate 19, limit cylinder 20, slot 21, annular boss 22, clamping block 23, sector-shaped limit plate 24, sliding through hole 25, elastic clamping plate 26, triangular ridge 27, reverse rotation stopper 28, ratchet wheel 29, ratchet groove 30, plastic column 31, display screen 32, sound sensor 33, vibration sensor 34, switch sensor 35, and perception sensor 36.

DETAILED DESCRIPTION OF THE EMBODIMENTS

As shown in FIG. 1-5, a manually controlled injection pen is used in the present disclosure and includes a pen cap 1, a refill 2, a needle 3, a refill sleeve 4, a main housing 5, a power assembly, a controller 6, a miniature battery 7 and a metering ring 8. The pen cap 1, the refill 2, the needle 3, the refill sleeve 4 and the main housing 5 are concentric and horizontally arranged in a left-right direction. A right end of the pen cap 1, a right end of the refill 2, a right end of the refill sleeve 4 and a left end of the main housing 5 are all open. The refill sleeve 4 fixedly sleeves the outside of the refill 2, and the pen cap 1 sleeves the outside of the refill sleeve 4 in a snapped mode. The needle 3 is fixedly mounted at a center of a left end of the refill sleeve 4, a right end of the needle 3 passes through the refill sleeve 4 and a left end of the refill 2 and is in communication with the interior of the refill 2, and a left end of the needle 3 is located at a left side of the refill sleeve 4. The left end of the refill sleeve 4 is in snapped connection to the needle cap 9 sleeving outside the needle 3, the right end of the refill 2 is connected to the left end of the main housing 5 by means of a connection assembly, and the interior of the refill 2 is slidably provided with an injection piston 10 in a sealed manner. The power assembly, the controller 6 and the miniature battery 7 are all mounted in the main housing 5. The metering ring 8 slidably sleeves the outside of the connection assembly. The power assembly drives the injection piston 10 to move leftwards. The miniature battery 7 is electrically connected to the power assembly and the controller 6 separately, and the controller 6 is connected to the power assembly in a signal manner.

The power assembly includes an electric motor 11, a gear box 12, a screw rod 13 and a hollow push rod 14. The electric motor 11 is fixedly mounted at an inner right side of the main housing 5. The gear box 12 is fixedly mounted in the inner middle of the main housing 5, and an outer circumference of the gear box 12 is fixedly clamped and fixed to an inner wall of the main housing 5. The screw rod 13 is rotatably arranged at an inner left side of the main housing 5 concentrically. A tubular column 15 is integrally formed in middle of a left end face of the gear box 12. A right end of the screw rod 13 extends into the tubular column 15 concentrically and is coaxially connected to a left end of a power output shaft at the center of the gear box 12 as one body, and a left end of the screw rod 13 passes through the connection assembly concentrically and is located at a right side of the right end of the refill 2. The hollow push rod 14 sleeves the outside of the screw rod 13 concentrically, a right end of an inner circle of the hollow push rod 14 is provided with an internal thread which is in a threaded fit connection to the outside of the screw rod 13, and a left end of the hollow push rod 14 extends into the refill 2 and is fixedly connected to a right end face of the injection piston 10. A power shaft of the electric motor 11 is horizontally arranged in the left-right direction, and a left end of the power shaft of the electric motor 11 is in transmission connection to a power input shaft of the gear box 12. The miniature battery 7 is electrically connected to the electric motor 11. The controller 6 is connected to the electric motor 11 in a signal manner. A switch key 16 for controlling the operation of the electric motor 11 is arranged in the middle of a right side face of the main housing 5.

The connection assembly includes a first connection sleeve 17 and a second connection sleeve 18. The first connection sleeve 17 fixedly sleeves the outside of the second connection sleeve 18 concentrically. A left end of the first connection sleeve 17 makes pressing contact with the right end of the refill 2. The right end of the refill sleeve 4 sleeves the left end of the first connection sleeve 17 in a threaded connection mode. The second connection sleeve 18 sleeves the outside of the hollow push rod 14 concentrically, a right end of the second connection sleeve 18 extends into the inner left side of the main housing 5 concentrically, and a ring-shaped limit plate 19 is integrally formed on an outer circle of the right end of the second connection sleeve 18. An inner circular edge of the left end of the main housing 5 is integrally provided with a limit cylinder 20 arranged concentrically and sleeving the right side of the second connection sleeve 18. The limit cylinder 20 is rotatably connected to the second connection sleeve 18, a right end of the limit cylinder 20 extends into the main housing 5 and makes pressing contact with an annular surface of a left side of the ring-shaped limit plate 19, a left end of the limit cylinder 20 is located on the left side of the main housing 5, and a left end edge of the limit cylinder 20 is provided with several slots 21 arranged in a circumferential array. An outer circumference of a right end of the push rod is integrally provided with an annular boss 22. A diameter of an inner cavity of the second connection sleeve 18 is greater than an outer diameter of the annular boss 22, and an inner diameter of a left end port of the second connection sleeve 18 is greater than an outer diameter of the push rod and is less than the outer diameter of the annular boss 22. The metering ring 8 is of a cylindrical structure which is opened left to right, the metering ring 8 slidingly sleeves the outside of the first connection sleeve 17 concentrically, an inner diameter of the metering ring 8 is greater than an outer diameter of the limit cylinder 20, a right end of the metering ring 8 is a bell mouth with a left portion smaller than a right portion, an inner circumference of the right side of the metering ring 8 is integrally provided with several clamping blocks 23 arranged in a circumferential array, and a sector-shaped limit plate 24 is integrally formed on the inner circumference of the metering ring 8 between two adjacent clamping blocks 23. Several sliding through holes 25 arranged in a circumferential array and located between the first connection sleeve 17 and the limit cylinder 20 are provided in the outer circumference of the right side of the second connection sleeve 18. The sector-shaped limit plates 24 corresponds one-to-one to the sliding through holes 25, a diameter of an inner circle of each of the sector-shaped limit plates 24 is less than an outer diameter of the first connection sleeve 17, and inner circle edges of the sector-shaped limit plates 24 are correspondingly slidingly arranged in the sliding through holes 25. The clamping blocks 23 engage with the slots 21 in a one-to-one corresponding manner. An elastic clamping plate 26 is integrally formed in the middle of a right side edge of each of the sliding through holes 25, and a triangular ridge 27 is arranged outside a left side edge of each of the elastic clamping plates 26. The inner circle edge of each of the sector-shaped limit plates 24 is an arc protrusion. Left side edges of the elastic clamping plates 26 are inserted into the metering ring 8 and are located on the left sides of the corresponding sector-shaped limit plates 24. The triangular ridges 27 are correspondingly clamped on the left sides of the corresponding sector-shaped limit plates 24.

A reverse rotation stopper 28 is fixedly connected to the left end face of the gear box 12 by means of several plastic columns 31, the right end of the second connection sleeve 18 sleeves a left end of the tubular column 15 in a rotating connection manner, a ratchet wheel 29 sleeving the outside of the tubular column 15 is fixedly connected to the right end of the second connection sleeve 18, the reverse rotation stopper 28 sleeves the outside of the ratchet wheel 29 in a rotating connection manner, and an inner circle of the reverse rotation stopper 28 is provided with ratchet grooves 30 matching and engaging with ratchets of an outer circle of the ratchet wheel 29.

A perception sensor 36 and a switch sensor 35 are arranged on a left side of the inner wall of the main housing 5, a sound sensor 33 and a vibration sensor 34 are arranged in the ratchet wheel 29, the perception sensor 36, the switch sensor 35, the sound sensor 33 and the vibration sensor 34 are all connected to the controller 6 by means of signal lines, the main housing 5 is provided with a charging interface (not shown in the figure) electrically connected to the miniature battery 7, and a display screen 32, the controller 6 is internally provided with a Bluetooth module, and the controller 6 is connected to the display screen 32 in a signal manner.

An acoustic method for precisely controlling and metering manual injection according to the present disclosure includes:

A, an injection pen enters an energy-saving mode when power is less than 20%, to allow manual injection operation merely; and when a user picks up the injection pen, a perception sensor 36 arranged on a left side of an inner wall of a main housing 5 sends a signal to a controller 6, and the controller 6 receives a signal of using the injection pen;

B, a pen cap 1 and a needle cap 9 are removed, and a metering ring 8 is pushed leftwards, to separate the metering ring 8 from a left end of the main housing 5, separate all clamping blocks 23 from slots 21, and move an outer triangular ridge 27 of a left side edge of each elastic clamping plate 26 leftwards to a right side of a corresponding sector-shaped limit plate 24, where the main housing 5 rotates relative to a second connection sleeve 18 and a refill 2 in this case; and a switch sensor 35 arranged on the left side of the inner wall of the main housing 5 monitors that the metering ring 8 moves leftwards, and transmits a signal to the controller 6, and the controller 6 receives the signal, to start a manual injection mode;

C, a user penetrates a needle 3 into a human body, holds a refill 2 sleeve and the metering ring 8 with one hand, holds the main housing 5 with the other hand, and rotates the main housing 5, to make the main housing 5 drive an internal gear box 12 to rotate, where a power output shaft of the gear box 12 is in a locked state in this case, the power output shaft of the gear box 12 drives a screw rod 13 to rotate, the screw rod 13 drives a hollow push rod 14 in threaded connection to the screw rod to move leftwards, the hollow push rod 14 pushes an injection piston 10 to move leftwards in the refill 2, and the injection piston 10 injects an insulin solution to be injected in the refill 2 into the human body;

D, during rotation of the main housing 5, a reverse rotation stopper 28 arranged on the inner wall of the main housing 5 rotates relative to the ratchet wheel, collision sounds and vibration are generated simultaneously by ratchet grooves 30 on an inner circle of the reverse rotation stopper 28 and ratchets on an outer circle of the ratchet wheel 29, where a sound sensor 33 and a vibration sensor 34 are arranged inside the ratchet wheel 29, the sound sensor 33 collects each collision sound signal, the vibration sensor 34 collects each vibration signal, the sound sensor 33 and the vibration sensor 34 transmit the collected signals to the controller 6, and the controller 6 classifies and recognize the sound and vibration signals through an internal algorithm, to record and save an insulin solution injection dosage, where each recognition success represents injection of 0.5 u of insulin solution, so as to accurately calculate the injection dosage during manual injection; and the injection dosage is displayed on a display screen 32, such that the user may be informed of the injection dosage only by observing a numerical value on the display screen 32; and E, after a target injection dosage is reached, rotation of the main housing 5 is stopped, and the metering ring 8 is moved rightwards and reset, so as to clamp all the clamping blocks 23 correspondingly into the slots 21, and further to keep the main housing 5 and the refill 2 fixed; and closing the needle cap 9 and pen cap 1.

Figure 4:
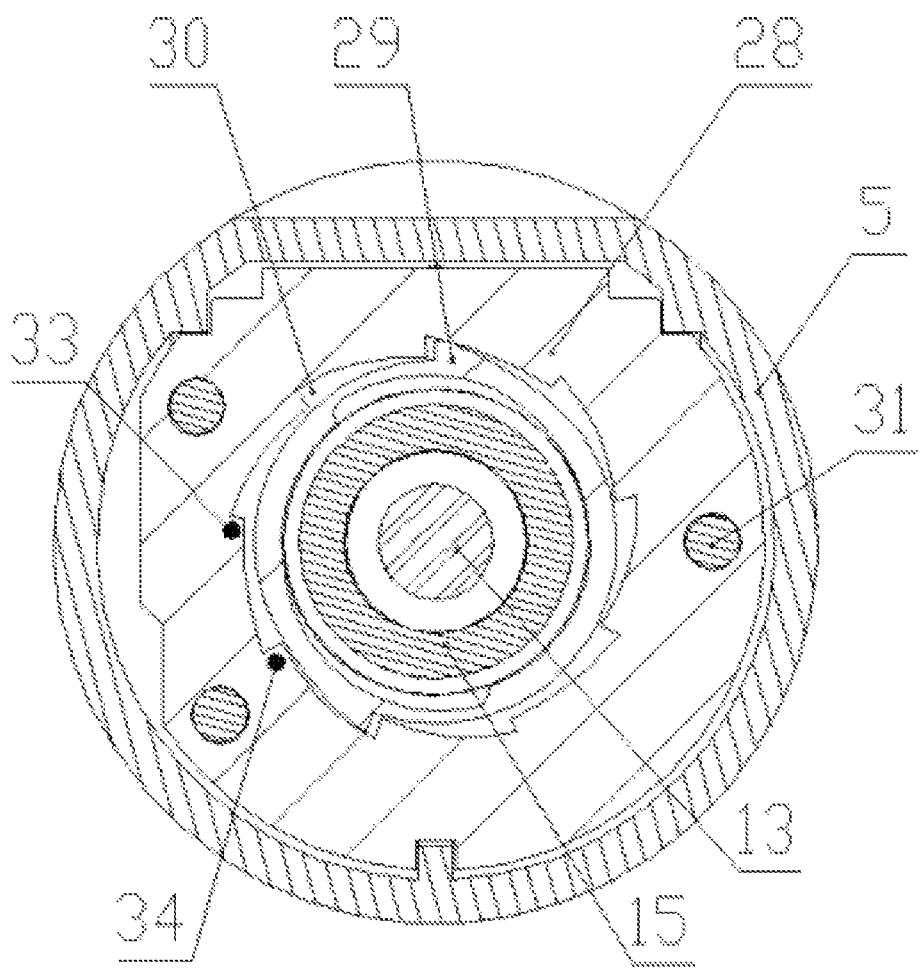
FIG. 4 is a schematic diagram of connection between a reverse rotation stopper and a ratchet wheel in a main housing of an injection pen.
Figure 5:
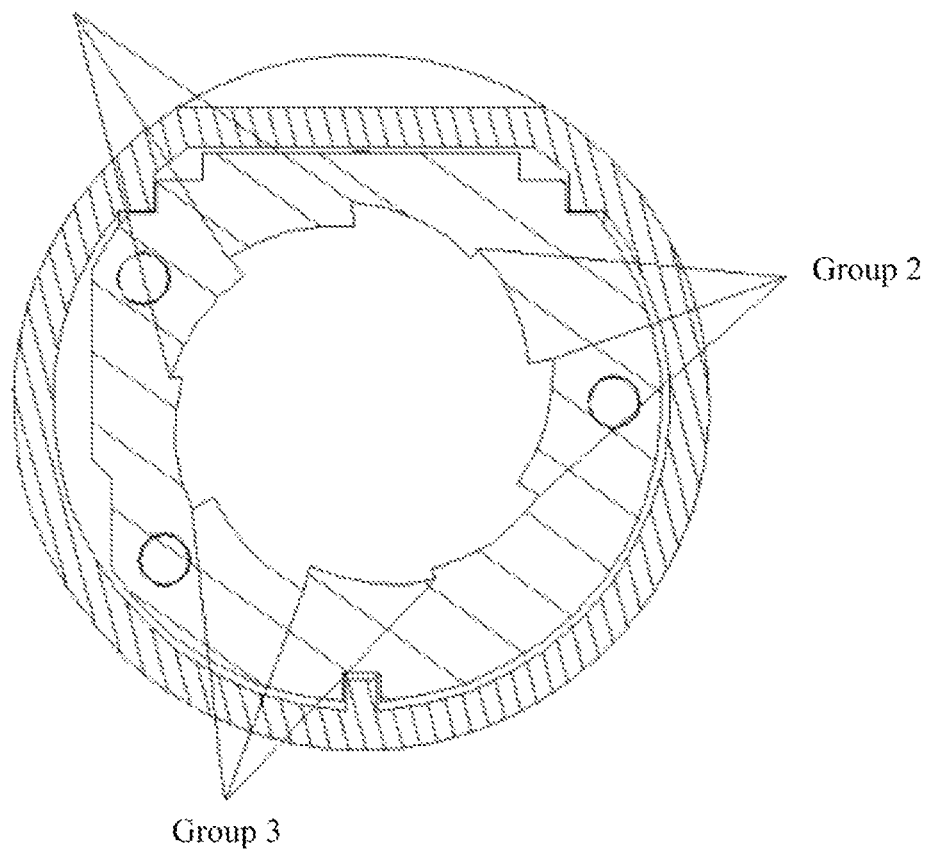
FIG. 5 is a schematic diagram of a shape of ratchet grooves of an injection pen.

As shown in FIGS. 4 and 5, the inner circle of the reverse rotation stopper 28 is uniformly provided with nine ratchet grooves 30 circumferentially, a central angle between two adjacent ratchet grooves 30 is 40°, the nine ratchet grooves 30 are divided into three groups in the same sequence, that is, group 1, group 2 and group 3, three adjacent ratchet grooves 30 serve as one group, depths of the three ratchet grooves 30 of each group successively increase in a clockwise direction, arrangement of the depths of the ratchet grooves 30 of the three groups is consistent, the outer circle of the ratchet wheel 29 are uniformly provided with three ratchets circumferentially, a central angle between two adjacent ratchets is 120°, when the ratchet wheel 29 rotates, the three ratchets collide with the ratchet grooves 30 of the same depth simultaneously, and the sounds and vibration generated by collisions between the ratchet grooves 30 and the ratchets are different every 40° of rotation of the ratchet grooves 30.

In step D, the internal algorithm of the controller 6 includes that feature processing is performed separately on the sound signals and the vibration signals generated when the ratchet grooves 30 on the inner circle of the reverse rotation stopper 28 collide with the ratchets on the outer circle of the ratchet wheel 29, processing with the internal algorithm of the controller 6 and classification and recognition with neural networks are performed, and then a recognition result of the sound signals, a recognition result of the vibration signals and detection time differences T between the sound signals and the vibration signals are uploaded to a support vector machine (SVM) separately for classification and recognition again.

A Mel-frequency cepstral coefficient (MFCC) method is used for a feature processing method of the sound signals generated when the ratchet grooves 30 on the inner circle of the reverse rotation stopper 28 collide with the ratchets on the outer circle of the ratchet wheel 29, an MFCC is extracted based on a Mel frequency, and a mapping relation between the Mel frequency and a normal Hertz frequency is shown in equation (1):

$$f_{mel} = 2595 \log_{10}\left(1 + \frac{f}{700}\right) \quad (1)$$

where $f_{mel}$ represents a Mel frequency in unit of MEL, and f represents a linear frequency in unit of Hz.

Figure 6:
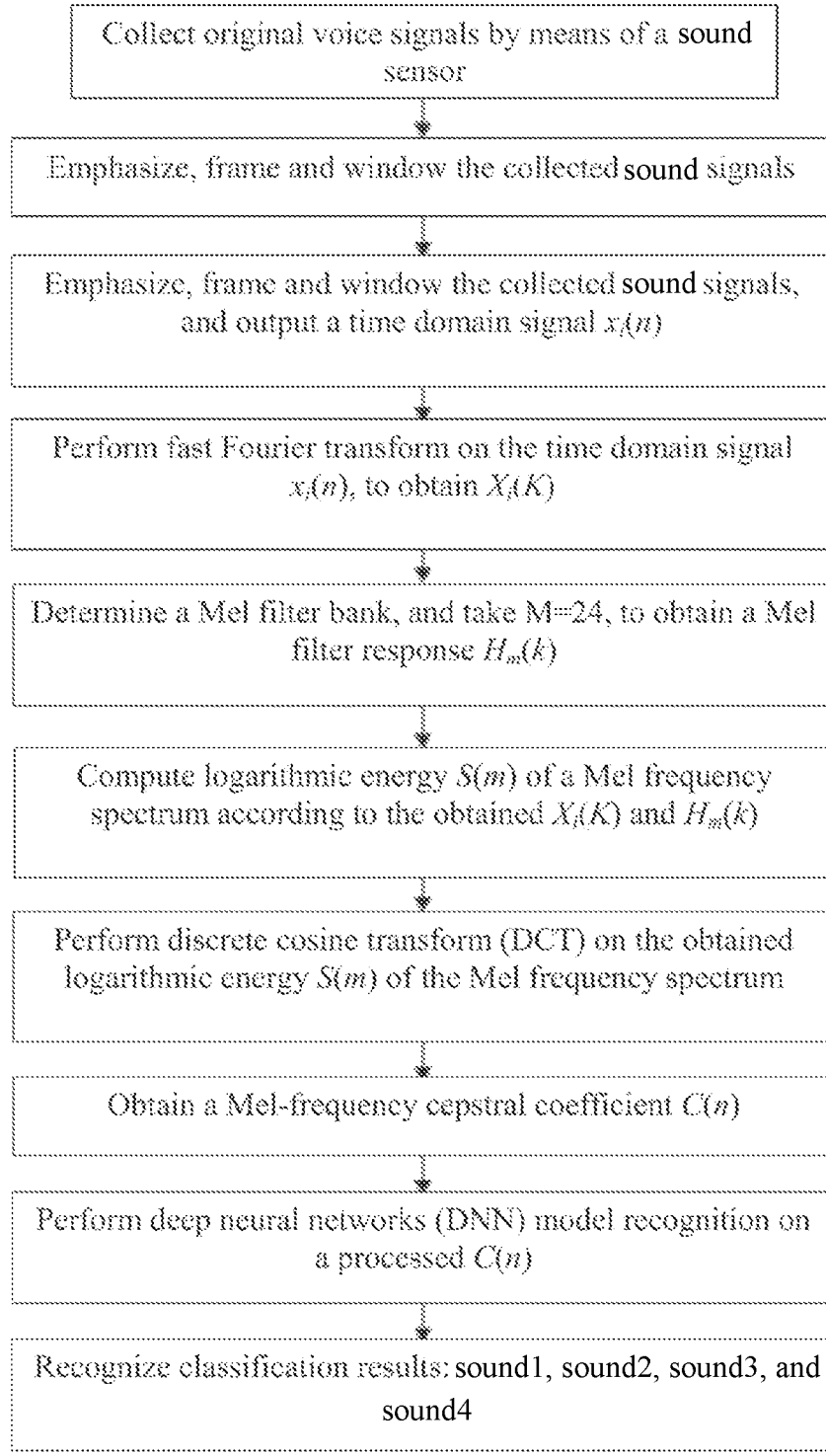
FIG. 6 is a flowchart of algorithmic processing of a sound signal according to the present disclosure.

As shown in FIG. 6, a particular flow of the Mel-frequency cepstral coefficient (MFCC) method includes:

1) the sound signals are collected: when the ratchet grooves 30 collide with the ratchets on the outer circle of the ratchet wheel 29, the sound signals of the collision sounds are transmitted to the interior of the controller 6 by means of the sound sensor 33 arranged in the ratchet wheel 29, where a collection time of each sound signal is 0.5 s;

2) the sounds are pre-processed: where a pre-processing process mainly includes that pre-emphasis, framing and windowing are performed on the sound signals; where the pre-emphasis on the sound signals usually uses a filtering method, in which an input signal x(n) passes through a high-pass filter, the filter is expressed as $V(n)=x(n)-a_1 x(n-1)$ in a time domain and expressed as $H(z)=1-a_1 z^{-1}$ in a frequency domain, where $0.9 \leq a_1 \leq 1.0$, and $a_1$ is a pre-emphasis coefficient and is preferably 0.97;

during the framing, a "short-time stationarity feature" of the sound signals is used to decompose each signal into several frames, each frame can be set as 20 ms, and a previous frame and a next frame overlap in half; and after the framing, the time domain signal x(n) is combined into $x_i(n)$, where i represents the relative frame number; and the windowing is to multiply an original function by a window function; assuming that x(n) is a time domain signal and w(n) is a window function, an N-point sequence $x_n(n)$ is derived from truncation of x(n) by w(n), as shown in equation (2):

$$x_n(n) = w(n) \times (n) \quad (2)$$

the present patent uses a Hamming window, as shown in equation (3) below:

$$W(n, a_2) = (1 - a_2) - a_2 \times \cos\left[\frac{2\pi n}{N-1}\right] \quad (3)$$

where $W(n, a_2)$ represents the window function, n=1, 2, 3, . . . . . . , N represents a serial number of a sampling point of the window function, and $a_2$ represents a middle position of a window and is preferably 0.46;

3) fast Fourier transform (FFT) is performed: FFT on $x_i(n)$ is performed to obtain $X_i(K)$, and computational equation (5) of $X_i(K)$ is obtained by combining equation (2) and computational equation (4) of discrete Fourier transform (DFT), where a Hamming window is used:

$$X_n\left(e^{j\frac{2k\pi}{N}}\right) = X_N(k) = \sum_{0}^{N-1} x(n) e^{-j\frac{2\pi kn}{N}}, k = 0, 1, 2, \ldots, N-1 \quad (4)$$

$$X_i(k) = \sum_{0}^{N-1} x_i(n) h(n) e^{-j\frac{2\pi kn}{N}}, k = 0, 1, \ldots, N-1 \quad (5)$$

where in equation (4), x(n) represents an original signal, $X_N(k)$ represents a coefficient after discrete cosine transform (DCT), and N represents the number of points of the original signal; and in equation (5), N represents a length of DFT, k represents a frequency, and h(n) represents a window function having the same length as the sample;

4) a Mel filter bank is determined: where the Mel frequency filter bank is a combination of a plurality of triangular band-pass filters $H_m(k)$ arranged according to a rule within a specified frequency spectrum range of an acoustic signal, $0 \leq m \leq M$, M is the number of filters, the number of filters is usually between 24-40, a center frequency of each of the triangular filters is f(m), and transfer function equation (6) is as follows:

$$H_m(k) = \begin{cases} \frac{k - f(m-1)}{f(m) - f(m-1)}, & f(m-1) \leq k \leq f(m) \\ \frac{f(m+1) - k}{f(m+1) - f(m)}, & f(m) \leq k \leq f(m+1) \\ 0, & k < f(m-1) \mid k > f(m+1) \end{cases} \quad (6)$$

where $H_m(k)$ is a frequency response of the Mel filters, and M is preferably 24;

5) logarithmic energy is computed: in order to make a Mel frequency spectrum obtained by means of the Mel filter bank more robust to noise and spectral estimation errors, the logarithmic energy of the Mel frequency spectrum is computed, where transfer function equation (7) from a linear frequency spectrum to a logarithmic frequency spectrum is as follows:

$$S(m) = \ln(\Sigma_0^{N-1} |X(k)|^2 H_m(k))(0 \leq m \leq M) \quad (7)$$

where X(k) is a linear frequency spectrum, S(m) is a logarithmic frequency spectrum, and m is the number of triangular band-pass filters;

6) discrete cosine transform is performed: discrete cosine transform (DCT) is performed on the obtained logarithmic frequency spectrum S(m) to be converted into the time domain, where the time domain is a cepstrum domain in this case, so as to obtain the Mel-frequency cepstral coefficient, and computational equation (8) thereof is as below:

$$C(n) = \sum_{0}^{M-1} S(m) \neq \cos\left(\frac{\pi n(m - 0.5)}{M}\right), 0 \leq n \leq L \quad (8)$$

where C(n) represents the MFCC of the nth filter, and L represents the dimension for extracting the feature parameter MFCC; and M represents the number of the Mel filter banks; and 7) classification with deep neural networks (DNN) is performed: static features from the MFCC of acoustic detection are input into a deep neural networks (DNN) model, a recognition result is output, and signals of the sound signals subjected to final processing and recognition are recorded as sound 1, sound 2, sound 3 and sound 4 separately, sound 1 being a coefficient of a sound generated by a collision between the ratchet groove 30 with the largest depth and the ratchet wheel 29, sound 2 being a coefficient of a sound generated by a collision between the ratchet groove 30 with the second largest depth and the ratchet wheel 29, sound 3 being a coefficient of a sound generated by a collision between the ratchet groove 30 with the least depth and the ratchet wheel 29, and sound 4 being a coefficient of a sound generated by other external collisions; and samples are trained based on the deep neural networks, where factors of the samples include the depths of the ratchet grooves 30, service life of an insulin syringe, a season for injecting insulin, an ambient temperature for injecting insulin, etc., 2000 groups of samples are trained, and 500 groups of each of sound 1, sound 2, sound 3 and sound 4 samples are trained. The deep neural networks (DNN) model is a conventional model and will not be repeated herein.

An empirical mode decomposition (EMD) method is used as a feature processing method of the vibration signals generated when the ratchet grooves 30 on the inner circle of the reverse rotation stopper 28 collide with the ratchets on the outer circle of the ratchet wheel 29, EMD decomposes a signal according to time scale features of the signal without setting a basis function, which is essentially a time-frequency analysis method, and is mainly used to complete decomposition of a non-stationary signal, to obtain a linear sum of a plurality of intrinsic mode functions (IFMs) and a trend term after decomposition, and the non-stationary signal y(t) may be expressed as:

$$y(t) = \sum_{0}^{n} IMF(t) + r(t) \quad (9)$$

where IMFi(t) represents an ith-order intrinsic mode function, and r(t) is a low-frequency pulsation, that is, the trend term.

Figure 7:
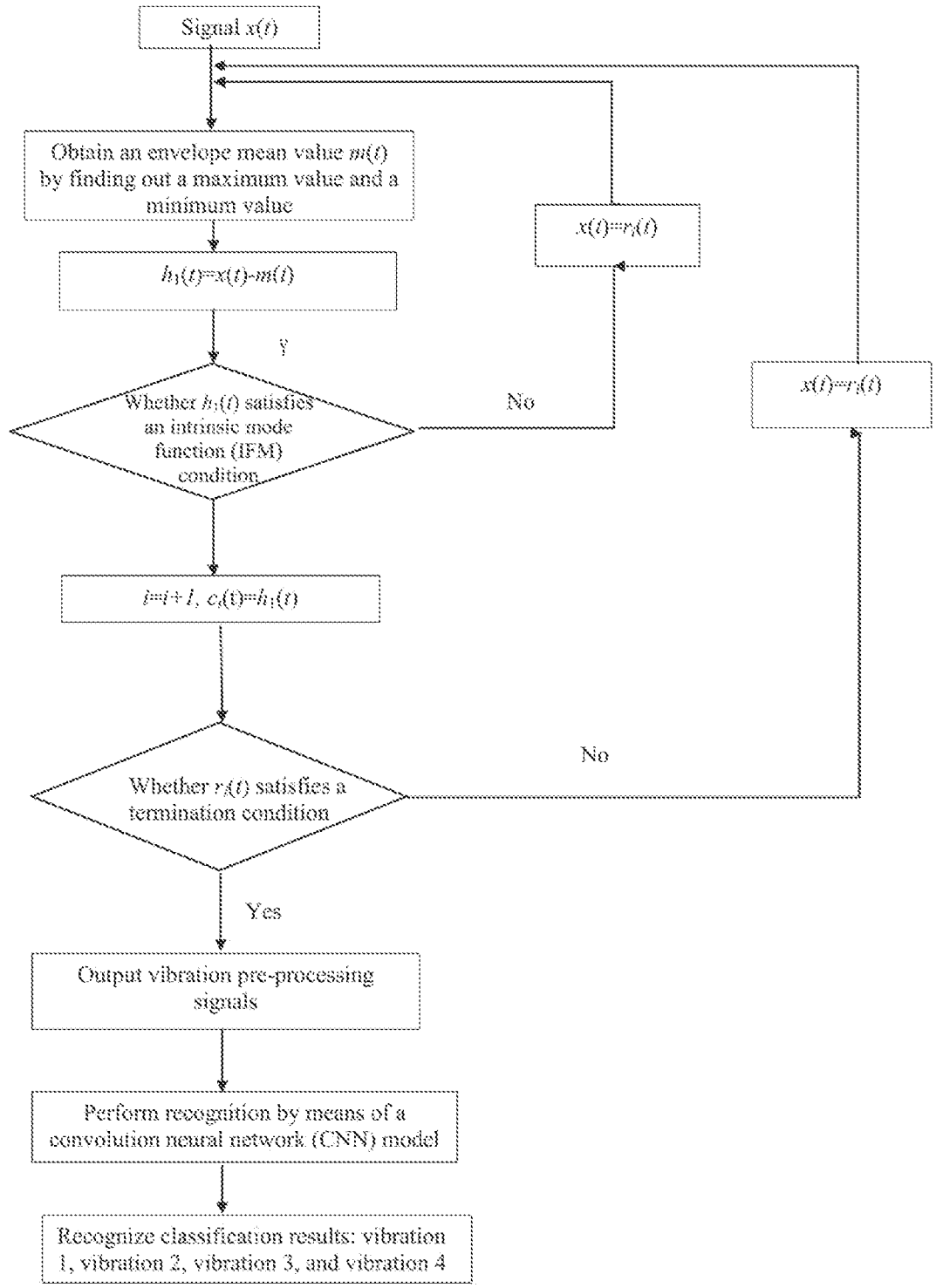
FIG. 7 is a flowchart of algorithmic processing of a vibration signal according to the present disclosure.

As shown in FIG. 7, a particular flow of the empirical mode decomposition (EMD) method includes that classification is performed on one vibration signal in sequence with EMD and a convolution neural network (CNN).

Particular steps for performing EMD on a signal include:
(1) the vibration signals are collected: when the ratchet grooves 30 collide with the ratchets on the outer circle of the ratchet wheel 29, the vibration signals of collisions are transmitted to the interior of the controller 6 by means of the vibration sensor 34 arranged in the ratchet wheel 29, where a collection time of each vibration signal is 0.5 s;
(2) all maximum value points and minimum value points of the vibration signals y(t) are found out, all the maximum value points and minimum value points are connected with curves to obtain an upper envelope line $e_{max}(t)$ and a lower envelope line $e_{min}(t)$, and a mean envelope function d(t) of the upper envelope line and the lower envelope line is computed;

$$d(t) = \frac{e_{max}(t) + e_{min}(t)}{2} \quad (10)$$

(3) Equation (10) records a difference between y(t) and d(t) as $h_1(t)$, and under the condition that $h_1(t)$ is not one IMF, the above process is continued until $h_{1k}(t)$ in a kth cycle is one IMF, which is recorded as $c_1(t)$;

(4) remaining signals y1(t) are obtained according to the decomposed IMF; and $$y_1(t)=y(t)-c_1(t) \quad (11)$$

(5) the above steps are repeated until an nth-order $h_n(t)$ becomes a monotonic sequence, and the trend term $r_n(t)$ is defined as $y_n(t)$.

A particular process for performing classification with a convolution neural network (CNN) includes: vibration pre-processing signals from vibration detection are input into a convolution neural network (CNN) model, a recognition result is output, and signals of the vibration signals subjected to final processing and recognition are recorded as vibration 1, vibration 2, vibration 3 and vibration 4 separately, vibration 1 being a vibration processing signal generated by a collision between the ratchet groove 30 with the largest depth and the ratchet wheel 29, vibration 2 being a vibration processing signal generated by a collision between the ratchet groove 30 with the second largest depth and the ratchet wheel 29, vibration 3 being a vibration processing signal generated by a collision between the ratchet groove 30 with the least depth and the ratchet wheel 29, and vibration 4 being a vibration processing signal generated by other external collisions; and samples are trained based on the deep neural networks, where factors of the samples include the depths of the ratchet grooves 30, service life of an insulin syringe, a season for injecting insulin, an ambient temperature for injecting insulin, etc., 2000 groups of samples are trained, and 500 groups of each of vibration 1, vibration 2, vibration 3 and vibration 4 samples are trained. The convolution neural network (CNN) model is a conventional model and will not be repeated herein.

Figure 8:
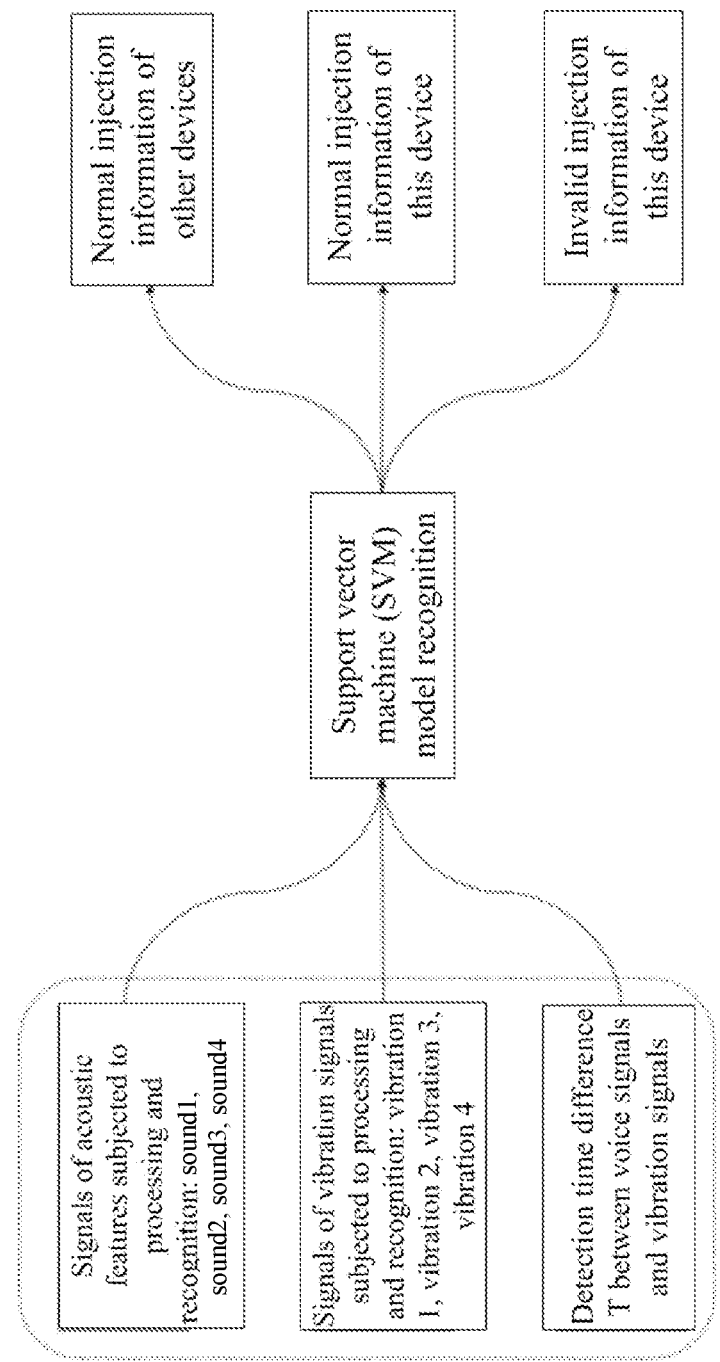
FIG. 8 is a flowchart of classification and recognition by a support vector machine (SVM) according to the present disclosure.

The step that a recognition result of the sound signals, a recognition result of the vibration signals and detection time differences T between the sound signals and the vibration signals are uploaded to a support vector machine (SVM) separately for classification and recognition again specifically includes:

since various kinds of sound signals and vibration signals exist in a process of manual injection of insulin, a multi-classification problem is involved, in a process of sound detection and vibration detection, samples of a SVM model are trained according to the actual situation due to different fundamental frequency periods of the sound signals and the vibration signals, the samples are trained based on the SVM model, where the factors of the samples include the depths of the ratchet grooves 30, the service life of an insulin syringe, a season for injecting insulin, the detection time differences T between the sound signals and the vibration signals, the ambient temperature for injecting insulin, etc., and 2000 groups of samples are training;

as shown in FIG. 8, sound 1, sound 2, sound 3 and sound 4 of the sound signals subjected to final processing and recognition and vibration 1, vibration 2, vibration 3 and vibration 4 of the vibration signals subjected to in final processing and recognition are input into the SVM model, the detection time differences T between the sound signals and the vibration signals are further input into the SVM model, and results are output by means of recognition by the SVM model, where the results include normal injection information, other syringe injection information and invalid injection information, so as to guarantee that the manual injection of insulin is accurately metered.

A manual injection metering cycle involves two situations, in the first situation, the cycle includes an entire time period from turning on of the switch sensor 35 to turning off of the switch sensor, and in the second situation, after reception of a signal that the switch sensor 35 is turned on, the manual injection mode of a manual injection device is not ended due to other situations, and the perception sensor 36 automatically ends metering when perceiving no external human contact in 10 minutes.

An injection dosage of insulin per time is shown in Equation 12:

$$S=0.5b_1+b_2\times 0 \tag{12}$$

where S is a manual injection cycle, $b_1$ is the number of detection recognition of the injection device, and b 2 is the number of invalid detection recognition.

The first situation is as follows: when using the insulin injection device for manual injection, a user removes the pen cap 1 and the needle cap 9 before use, and then pushes the metering ring 8 leftwards, to separate the metering ring 8 from the left end of the main housing 5, and in this case, the switch sensor 35 transmits a manual injection start signal, to start the injection cycle; and after manual injection is completed, the patient pushes the metering ring 8 rightwards, to attach the metering ring 8 to the left end of the main housing 5, and in this case, the switch sensor 35 transmits a manual injection end signal, to end the injection cycle.

The second situation is as follows: when using the insulin injection device for manual injection, a patient removes the pen cap 1 and the needle cap 9 before use, and then pushes the metering ring 8 leftwards, to separate the metering ring 8 from the left end of the main housing 5, and in this case, the switch sensor 35 transmits a manual injection start signal, to start the injection cycle; and when the patient has an emergency during injection, manual injection is not completed and the manual injection mode is not ended, and in this case, the perception sensor 36 automatically ends the metering cycle when perceiving no touch on the injection device in 10 minutes by the patient.

The embodiment does not limit the shape, material, structure, etc. of the present disclosure in any form, and any simple amendment, equivalent change and modification of the above embodiment according to the technical spirit of the present disclosure fall within the scope of the protection of the technical solution of the present disclosure.

The invention claimed is:

1. An acoustic method for precisely controlling and metering manual injection, comprising:

step A, making an injection pen enter an energy-saving mode when power is less than 20% such that the injection pen is configured for manual injection operation only; and when a user picks up the injection pen, sending a signal to a controller (6) by a perception sensor (36), arranged on a left side of an inner wall of a main housing (51 and receiving, by the controller (6), a signal of using the injection pen, wherein the perception sensor (36) is configured to detect a state of the injection pen; automatically ends metering when perceiving no external human contact in 10 minutes and is connected to the controller (6) by means of signal lines;

step B, removing a pen cap (11 and a needle cap (9), and pushing a metering ring (8), to separate the metering ring (8) from a left end of the main housing (5), separate all clamping blocks (23) from slots (21), and move an outer triangular ridge (27) of a left side edge of each elastic clamping plate (26) to a right side of a corresponding sector-shaped limit plate (24), wherein a first connection sleeve (17) is fixedly and concentrically sleeved on an outside of a second connection sleeve, the main housing (5) rotates relative to the second connection sleeve (18) and a refill (2); and monitoring that the metering ring (8) moves and transmitting a signal to the controller (6) by a switch sensor (35) arranged on the left side of the inner wall of the main housing (5), and receiving the signal by the controller (6), to start a manual injection mode;

step C, penetration of a human body via a needle (3) by a user, holding a refill sleeve (4) and the metering ring (8) with one hand, holding the main housing (5) with the other hand, rotating the main housing (5), to make the main housing (5) drive an internal gear box (12), to rotate, wherein a power output shaft of the gear box (12) is in a locked state driving a screw rod (13) to rotate by the power output shaft of the gear box (12) driving a hollow push rod (14) in threaded connection to the screw rod (13) by the screw rod (13) to move, pushing an injection piston (10) by the hollow push rod (14) to move in the refill (2), and injecting an insulin solution in the refill (2) into the human body by the injection piston (10);

step D, during rotation of the main housing (5), arranging a reverse rotation stopper (28) on the inner wall of the main housing (5) rotate relative to a ratchet wheel (29), generating sounds and vibration simultaneously by collisions between (a) ratchet grooves (30) on an inner circle of the reverse rotation stopper (28) and (b) ratchets on an outer circle of the ratchet wheel (29), wherein a sound sensor (33) and a vibration sensor 134) are arranged inside the ratchet wheel (29), collecting each collision sound signal by the sound sensor (33), collecting each vibration signal by the vibration sensor (34), transmitting collected signals to the controller (6) by the sound sensor (33) and the vibration sensor (34), and classifying and recognizing the sound and vibration signals by the controller (6) through an internal algorithm, to record and save an insulin solution injection dosage, wherein each success of recognizing represents injection of 0.5 u of insulin solution, so as to accurately calculate the injection dosage during manual injection; and displaying the injection dosage on a display screen (32), such that the user can be informed of the injection dosage only by observing a numerical value on the display screen (32); and step E, after a target injection dosage is reached, stopping rotating the main housing (5), moving the metering ring (8), and resetting the metering ring (8), so as to clamp all the clamping blocks (23) correspondingly into the slots (21), and further to keep the main housing (5) and the refill (2) fixed; and closing the needle cap (9) and pen cap (1);

wherein the pen cap (1), the refill (2), the needle, the refill sleeve (4) and the main housing (5) are concentric and horizontally arranged in a left-right direction;

a right end of the pen cap (11, a right end of the refill (21, a right end of the refill sleeve (4) and a left end of the main housing (5) are all open;

the refill sleeve (4) fixedly sleeves the outside of the refill (2), and the pen cap (1) sleeves the outside of the refill sleeve (4) in a snapped mode;

the needle (3) is fixedly mounted at a center of a left end of the refill sleeve (4), a right end of the needle (3) passes through the refill sleeve (4) and a left end of the refill (2) and is in communication with the interior of the refill (2), and a left end of the needle (3) is located at a left side of the refill sleeve (4);

the left end of the refill sleeve (4) is in snapped connection to the needle cap (9) sleeving outside the needle (3), the right end of the refill (2) is connected to the left end of the main housing (5) by means of a connection assembly, and the interior of the refill (2) is slidably provided with an injection piston (10) in a sealed manner;

the power assembly, the controller (6) and the miniature battery (7) are all mounted in the main housing (5);

the metering ring (8) slidably sleeves the outside of the connection assembly;

the power assembly drives the injection piston (10) to move;

the miniature battery (7) is electrically connected to the power assembly and the controller (6) separately, and the controller (6) is connected to the power assembly in a signal manner;

the power assembly comprises an electric motor (11), a gear box (12), a screw rod (13) and a hollow push rod (14;

the electric motor (11) is fixedly mounted at an inner right side of the main housing LSI;

the gear box (12) is fixedly mounted in the inner middle of the main housing LSI and an outer circumference of the gear box (12) is fixedly clamped and fixed to an inner wall of the main housing (5);

the screw rod (13) is rotatably arranged at an inner left side of the main housing (5) concentrically;

a tubular column (15) is integrally formed in middle of a left end face of the gear box (12);

a right end of the screw rod (13) extends into the tubular column (15) concentrically and is coaxially connected to a left end of a power output shaft at the center of the gear box (12) as one body, and a left end of the screw rod (13) passes through the connection assembly concentrically and is located at a right side of the right end of the refill (2);

the hollow push rod (14) sleeves the outside of the screw rod (13) concentrically, a right end of an inner circle of the hollow push rod (14) is provided with an internal thread which is in a threaded fit connection to the outside of the screw rod (13), and a left end of the hollow push rod (14) extends into the refill (2) and is fixedly connected to a right end face of the injection piston (10);

a power shaft of the electric motor (11) is horizontally arranged in the left-right direction, and a left end of the power shaft of the electric motor (11) is in transmission connection to a power input shaft of the gear box (12); the miniature battery (7) is electrically connected to the electric motor (11);

the controller (6) is connected to the electric motor (11) in a signal manner; a switch key (16) for controlling the operation of the electric motor (11) is arranged in the middle of a right-side face of the main housing (5);

wherein, the connection assembly comprises a first connection sleeve (17) and a second connection sleeve (18);

the first connection sleeve (17) fixedly sleeves the outside of the second connection sleeve (18) concentrically;

a left end of the first connection sleeve (17) makes pressing contact with the right end of the refill (2); the right end of the refill sleeve (4) sleeves the left end of the first connection sleeve (17) in a threaded connection mode;

the second connection sleeve (18) sleeves the outside of the hollow push rod (14 concentrically, a right end of the second connection sleeve (18) extends into the inner left side of the main housing (5) concentrically, and a ring-shaped limit plate (19) is metering ring integrally formed on an outer circle of the right end of the second connection sleeve (18);

an inner circular edge of the left end of the main housing (5) is integrally provided with a limit cylinder (20) arranged concentrically and sleeving the right side of the second connection sleeve (18);

the limit cylinder (20) is rotatably connected to the second connection sleeve (18), a right end of the limit cylinder (20) extends into the main housing (51 and makes pressing contact with an annular surface of a left side of the ring-shaped limit plate (19), a left end of the limit cylinder (20) is located on the left side of the main housing (5), and a left end edge of the limit cylinder (20) is provided with several slots (211 arranged in a circumferential array;

an outer circumference of a right end of the push rod is integrally provided with an annular boss (22);

a diameter of an inner cavity of the second connection sleeve (18) is greater than an outer diameter of the annular boss (22), and an inner diameter of a left end port of the second connection sleeve (18) is greater than an outer diameter of the push rod and is less than the outer diameter of the annular boss (22);

the metering ring (8) is of a cylindrical structure which is opened left to right, the metering ring (8) slidingly sleeves the outside of the first connection sleeve (17) concentrically, an inner diameter of the metering ring (8) is greater than an outer diameter of the limit cylinder (20), a right end of the metering ring (8) is a bell mouth with a left portion smaller than a right portion, an inner circumference of the right side of the metering ring (8) is integrally provided with several clamping blocks (23) arranged in a circumferential array, and a sector-shaped limit plate (24) is integrally formed on the inner circumference of the metering ring (8) between two adjacent clamping blocks (23);

sliding through holes (25) arranged in a circumferential array and located between the first connection sleeve (17) and the limit cylinder (20) are provided in the outer circumference of the right side of the second connection sleeve (18);

the sector-shaped limit plates (24) corresponds one-to-one to the sliding through holes (25), a diameter of an inner circle of each of the sector-shaped limit plates (24) is less than an outer diameter of the first connection sleeve (17), and inner circle edges of the sector-shaped limit plates (24) are correspondingly slidingly arranged in the sliding through holes (25);

the clamping blocks (23) engage with the slots (21) in a one-to-one corresponding manner; an elastic clamping plate (26) is integrally formed in the middle of a right side edge of each of the sliding through holes (25), and a triangular ridge (27) is arranged outside a left side edge of each of the elastic clamping plates (26);

the inner circle edge of each of the sector-shaped limit plates (24) is an arc protrusion; left side edges of the elastic clamping plates (26) are inserted into the metering ring (8) and are located on the left sides of the corresponding sector-shaped limit plates (24);

the triangular ridges (27) are correspondingly clamped on the left sides of the corresponding sector-shaped limit plates (24);

a reverse rotation stopper (28) is fixedly connected to the left end face of the gear box (12) by means of several plastic columns (31), the right end of the second connection sleeve (18) sleeves a left end of the tubular column (15) in a rotating connection manner, a ratchet wheel (29) sleeving the outside of the tubular column (15) is fixedly connected to the right end of the second connection sleeve (18), the reverse rotation stopper (28) sleeves the outside of the ratchet wheel (29) in a rotating connection manner, and an inner circle of the reverse rotation stopper (28) is provided with ratchet grooves (30) matching and engaging with ratchets of an outer circle of the ratchet wheel (29);

a perception sensor (36) and a switch sensor (35) are arranged on a left side of the inner wall of the main housing (5), a sound sensor (33) and a vibration sensor (34) are arranged in the ratchet wheel (29), the perception sensor (36), the switch sensor (35), the sound sensor (33) and the vibration sensor (34) are all connected to the controller (6) by means of signal lines, the main housing (5) is provided with a charging interface (not shown in the figure) electrically connected to the miniature battery (7), and a display screen (32), the controller (6) is internally provided with a Bluetooth module, and the controller (6) is connected to the display screen (32) in the signal manner.

2. The acoustic method for precisely controlling and metering manual injection according to claim 1, wherein the inner circle of the reverse rotation stopper (28) is uniformly provided with nine ratchet grooves (30) circumferentially, a central angle between two adjacent ratchet grooves (30) is 40°, the nine ratchet grooves (30) are divided into three groups in the same sequence, the three groups comprising group 1, group 2 and group 3, three adjacent ratchet grooves (30) serve as one group, depths of the three ratchet grooves (30) of each group are different and successively increase in a clockwise direction, the depths of the ratchet grooves (30) of the three groups are consistently arranged, the outer circle of the ratchet wheel (29) is uniformly provided with three ratchets circumferentially, a central angle between two adjacent ratchets is 120°, when the ratchet wheel (29) rotates, the three ratchets collide with the ratchet grooves (30) of the same depth simultaneously, and the sounds and vibration generated by collisions between the ratchet grooves (30) and the ratchets are different every 40° of rotation of the ratchet grooves (30); and in the step D, the internal algorithm of the controller (6) comprises performing feature processing separately on the sound signals and the vibration signals generated when the ratchet grooves (30) on the inner circle of the reverse rotation stopper (28) collide with the ratchets on the outer circle of the ratchet wheel (29), performing processing with the internal algorithm of the controller (6) and classification and recognition with neural networks, and then uploading a recognition result of the sound signals, a recognition result of the vibration signals and detection time differences between the sound signals and the vibration signals to a support vector machine (SVM) separately for classification and recognition.

3. The acoustic method for precisely controlling and metering manual injection according to claim 2, wherein in the step D, a Mel-frequency cepstral coefficient (MFCC) method is used as a feature processing method of the sound signals generated when the ratchet grooves (30) on the inner circle of the reverse rotation stopper (28) collide with the ratchets on the outer circle of the ratchet wheel (29), an MFCC is extracted based on a Mel frequency, and a mapping relation between the Mel frequency and a normal Hertz frequency is shown in equation (1):

$$f_{mel} = 2595 \log_{10}\left(1 + \frac{f}{700}\right) \quad (1)$$

wherein $f_{mel}$ represents a Mel frequency in unit of MEL, and f represents a linear frequency in unit of Hz;

a particular flow of the Mel-frequency cepstral coefficient (MFCC) method comprises:

1) Collecting the sound signals: when the ratchet grooves (30) collide with the ratchets on the outer circle of the ratchet wheel (29), transmitting the sound signals of the collision sounds to the interior of the controller (6) by means of the sound sensor arranged in the ratchet wheel (29), wherein a collection time of each sound signal is 0.2 s–0.5 s;

2) Pre-processing the sounds: wherein a pre-processing process mainly comprises performing pre-emphasis, framing and windowing on the sound signals; wherein the pre-emphasis on the sound signals usually uses a filtering method, in which an input signal x(n) passes through a high-pass filter, the filter is expressed as V(n)=x(n)−$a_1$x(n−1) in a time domain and expressed as H(z)=1−$a_1 z^{-1}$ in a frequency domain, wherein 0.9≤$a_1$≤1.0, and $a_1$ is a pre-emphasis coefficient and is preferably 0.97;

during the framing, a "short-time stationarity feature" of the sound signals is used to decompose each signal into several frames, each frame can be set as 20 ms, and a previous frame and a next frame overlap in half; and after the framing, the time domain signal x(n) is combined into $x_i$(n), wherein i represents the relative frame number; and the windowing is to multiply an original function by a window function; assuming that x(n) is a time domain signal and w(n) is a window function, an N-point sequence $x_n$(n) is derived from truncation of x(n) by w(n), as shown in equation (2):

$$x_n(n) = w(n)x(n) \quad (2)$$

the present patent uses a Hamming window, as shown in equation (3) below:

$$W(n, a_2) = (1 - a_2) - a_2 \times \cos\left[\frac{2\pi n}{N - 1}\right] \quad (3)$$

wherein W(n,$a_2$) represents the window function, n=1, 2, 3, ..., N represents a serial number of a sampling point of the window function, and $a_2$ represents a middle position of a window and is preferably 0.46;

3) Performing fast Fourier transform (FFT): performing FFT on $x_i$(n) to obtain $X_i$(K), and obtaining computational equation (5) of $X_i$(K) by combining equation (2) and computational equation (4) of discrete Fourier transform (DFT), wherein a Hamming window is used:

$$X_n\left(e^{j\frac{2k\pi}{N}}\right) = X_N(k) = \sum_0^{N-1} x(n) e^{-j\frac{2\pi kn}{N}}, k = 0, 1, 2, \ldots, N - 1 \quad (4)$$

$$X_i(k) = \sum_0^{N-1} x_i(n) h(n) e^{-j\frac{2\pi kn}{N}}, k = 0, 1, \ldots, N - 1 \quad (5)$$

wherein in equation (4), x(n) represents an original signal, $X_N$(k) represents a coefficient after discrete cosine transform (DCT), and N represents the number of points of the original signal; and in equation (5), N represents a length of DFT, k represents a frequency, and h(n) represents a window function having the same length as the sample;
4) Determining a Mel filter bank: wherein the Mel frequency filter bank is a combination of a plurality of triangular band-pass filters $H_m(k)$ arranged according to a rule within a specified frequency spectrum range of an acoustic signal, $0 \leq m \leq M$, M is the number of filters, the number of filters is usually between 24-40, a center frequency of each of the triangular filters is f(m), and transfer function equation (6) is as follows:

$$H_m(k) = \begin{cases} \dfrac{k - f(m-1)}{f(m) - f(m-1)}, & f(m-1) \leq k \leq f(m) \\ \dfrac{f(m+1) - k}{f(m+1) - f(m)}, & f(m) \leq k \leq f(m+1) \\ 0, & k < f(m-1) \mid k > f(m+1) \end{cases} \quad (6)$$

wherein $H_m(k)$ is a frequency response of the Mel filters;
5) Computing logarithmic energy: in order to make a Mel frequency spectrum obtained by means of the Mel filter bank more robust to noise and spectral estimation errors, computing the logarithmic energy of the Mel frequency spectrum, wherein transfer function equation (7) from a linear frequency spectrum to a logarithmic frequency spectrum is as follows:

$$S(m) = \ln(\Sigma_0^{N-1} |X(k)|^2 H_m(k))(0 \leq m \leq M) \quad (7)$$

wherein X(k) is a linear frequency spectrum, S(m) is a logarithmic frequency spectrum, and m is the number of triangular band-pass filters;
6) Performing discrete cosine transform: performing discrete cosine transform (DCT) on the obtained logarithmic frequency spectrum S(m) to be converted into the time domain, wherein the time domain is a cepstrum domain so as to obtain the Mel-frequency cepstral coefficient, and computational equation (8) thereof is as below:

$$C(n) = \sum_0^{M-1} S(m) \neq \cos\left(\frac{\pi n(m - 0.5)}{M}\right), \quad 0 \leq n \leq L \quad (8)$$

wherein C(n) represents the MFCC of the nth filter, and L represents the dimension for extracting the feature parameter MFCC; M represents the number of the Mel filter banks; and the above is a flow for extracting the Mel-frequency cepstral coefficient (MFCC); and
7) Performing classification with deep neural networks (DNN): inputting static features of the MFCC from acoustic detection into a deep neural networks (DNN) model, outputting a recognition result, and recording signals of the sound signals subjected to final processing and recognition as sound 1, sound 2, sound 3 and sound 4 separately, sound 1 being a coefficient of a sound generated by a collision between the ratchet groove (30) with the largest depth and the ratchet wheel (29), sound 2 being a coefficient of a sound generated by a collision between the ratchet groove (30) with the second largest depth and the ratchet wheel (29), sound 3 being a coefficient of a sound generated by a collision between the ratchet groove (30) with the least depth and the ratchet wheel (29), and sound 4 being a coefficient of a sound generated by other external collisions; and training samples based on the deep neural networks, wherein factors of the samples comprise the depths of the ratchet grooves (30), service life of an insulin syringe, a season for injecting insulin, and an ambient temperature for injecting insulin, training 2000 groups of samples, and training 500 groups of each of sound 1, sound 2, sound 3 and sound 4 samples.

4. The acoustic method for precisely controlling and metering manual injection according to claim 2, wherein an empirical mode decomposition (EMD) method is used as a feature processing method of the vibration signals generated when the ratchet grooves (30) on the inner circle of the reverse rotation stopper (28) collide with the ratchets on the outer circle of the ratchet wheel (29), EMD decomposes a signal according to time scale features of the signal without setting a basis function, comprising a time-frequency analysis method, and is used to complete decomposition of a non-stationary signal, to obtain a linear sum of a plurality of intrinsic mode functions (IFMs) and a trend term after decomposition, and the non-stationary signal y(t) can be expressed as:

$$y(t) = \sum_0^n IMF_i(t) + r(t) \quad (9)$$

wherein $IMF_i(t)$ represents an ith-order intrinsic mode function, and r(t) is a low-frequency pulsation, and the trend term; and
a particular flow of the empirical mode decomposition (EMD) method comprises performing classification on one vibration signal in sequence with EMD and a convolution neural network (CNN).

5. The acoustic method for precisely controlling and metering manual injection according to claim 4, wherein particular steps for performing EMD on a signal comprise:
(1) collecting the vibration signals: when the ratchet grooves (30) collide with the ratchets on the outer circle of the ratchet wheel (29), transmitting the vibration signals of collisions to the interior of the controller by means of the vibration sensor (34 arranged in the ratchet wheel (29), wherein a collection time of each vibration signal is 0.2 s-0.5 s;
(2) finding out all maximum value points and minimum value points of the vibration signals y(t), connecting all the maximum value points and minimum value points with curves to obtain an upper envelope line $e_{max}(t)$ and a lower envelope line $e_{min}(t)$, and computing a mean envelope function d(t) of the upper envelope line and the lower envelope line;

$$d(t) = \frac{e_{max}(t) + e_{min}(t)}{2} \quad (10)$$

(3) recording a difference between y(t) and d(t) as $h_1(t)$, and under the condition that $h_1(t)$ is not one IMF, continuing the above process until $h_{1k}(t)$ in a kth cycle is one IMF, which is recorded as $c_1(t)$;
(4) obtaining remaining signals $y_1(t)$ according to the decomposed IMF; and $$y_1(t) = y(t) - c_1(t) \quad (11)$$

(5) repeating the above steps until an nth-order $h_n(t)$ becomes a monotonic sequence, and defining the trend term $r_n(t)$ as $y_n(t)$.

6. The acoustic method for precisely controlling and metering manual injection according to claim 5, wherein a particular process for performing classification with a convolution neural network (CNN) comprises: inputting vibration pre-processing signal from vibration detection into a convolution neural network (CNN) model, outputting a recognition result, and recording signals of the vibration signals subjected to final processing and recognition as vibration 1, vibration 2, vibration 3 and vibration 4 separately, vibration 1 being a vibration processing signal generated by a collision between the ratchet groove (30) with the largest depth and the ratchet wheel (29), vibration 2 being a vibration processing signal generated by a collision between the ratchet groove (30) with the second largest depth and the ratchet wheel (29), vibration 3 being a vibration processing signal generated by a collision between the ratchet groove (30) with the least depth and the ratchet wheel (29) and vibration 4 being a vibration processing signal generated by other external collisions; and training samples based on the deep neural networks, wherein factors of the samples comprise the depths of the ratchet grooves (30), service life of an insulin syringe, a season for injecting insulin, and an ambient temperature for injecting insulin, training 2000 groups of samples, and training 500 groups of each of vibration 1, vibration 2, vibration 3 and vibration 4 samples.

7. The acoustic method for precisely controlling and metering manual injection according to claim 6, wherein the uploading a recognition result of the sound signals, a recognition result of the vibration signals and detection time differences T between the sound signals and the vibration signals to a support vector machine (SVM) separately for classification and recognition again specifically comprises:

since sound signals and vibration signals are of various kinds and exist in a process of manual injection of insulin, a multi-classification problem is involved, in a process of sound detection and vibration detection, training samples of a SVM model according to the actual situation due to different fundamental frequency periods of the sound signals and the vibration signals, training the samples based on the SVM model, wherein the factors of the samples comprise the depths of the ratchet grooves (30), the service life of an insulin syringe, a season for injecting insulin, the detection time differences T between the sound signals and the vibration signals, and the ambient temperature for injecting insulin, and training 2000 groups of samples; and inputting sound 1, sound 2, sound 3 and sound 4 of the sound signals subjected to final processing and recognition and vibration 1, vibration 2, vibration 3 and vibration 4 of the vibration signals subjected to final processing and recognition into the SVM model, further inputting the detection time differences T between the sound signals and the vibration signals into the SVM model, and outputting results by means of recognition by the SVM model, wherein the results comprise normal injection information, other syringe injection information and invalid injection information, so as to guarantee that the manual injection of insulin is accurately metered; wherein a manual injection metering cycle involves two situations, the first situation is as follows: the cycle comprises an entire time period from turning on of the switch sensor (35) to turning off of the switch sensor (35), and the second situation is as follows: after reception of a signal that the switch sensor (35) is turned on, the manual injection mode of a manual injection device is not ended due to other situations, and the perception sensor (36) automatically ends metering when perceiving no external human contact in 10 minutes; and an injection dosage of insulin per time is shown in Equation 12:

$$S = 0.5b_1 + b_2 \times 0 \qquad (12)$$

wherein S is an injection dosage per injection cycle, b1 is the number of detection recognition of the injection device, and b2 is the number of invalid detection recognition.

8. The acoustic method for precisely controlling and metering manual injection according to claim 7, wherein the first situation is as follows: when using the insulin injection device for manual injection, a user removes the pen cap (1) and the needle cap (9) before use, and then pushes the metering ring (8), to separate the metering ring (8) from the left end of the main housing (5), and the switch sensor (35) transmits a manual injection start signal, to start the injection cycle; and after manual injection is completed, the patient pushes the metering ring (8), to attach the metering ring (8) to the left end of the main housing (5), and the switch sensor (35) transmits a manual injection end signal, to end the injection cycle; and the second situation is as follows: when using the insulin injection device for manual injection, a patient removes the pen cap (1) and the needle cap (9) before use, and then pushes the metering ring (8), to separate the metering ring (8) from the left end of the main housing (5), and the switch sensor (35) transmits a manual injection start signal, to start the injection cycle; and when the patient has an emergency during injection, manual injection is not completed and the manual injection mode is not ended, and the perception sensor (36) automatically ends the metering cycle when perceiving no touch on the injection device in 10 minutes by the patient.

\* \* \* \* \*